United States Patent [19]

Fite et al.

[11] 3,973,121

[45] Aug. 3, 1976

[54] DETECTOR FOR HEAVY IONS FOLLOWING MASS ANALYSIS

[76] Inventors: Wade L. Fite, 305 Pasadena Drive, Pittsburgh, Pa. 15215; Richard L. Myers, Rte. 1, Box 225, Harmony, Pa. 16037

[22] Filed: Apr. 29, 1974

[21] Appl. No.: 465,163

Related U.S. Application Data

[63] Continuation-in-part of Ser. No. 319,442, Dec. 29, 1972, Pat. No. 3,808,433.

[52] U.S. Cl. .............................. 250/292; 250/281; 250/282; 250/425
[51] Int. Cl.² ........................................ H01J 39/34
[58] Field of Search .......... 250/251, 425, 292, 282, 250/281

[56] References Cited
UNITED STATES PATENTS

| | | | |
|---|---|---|---|
| 3,258,713 | 6/1966 | George | 250/251 |
| 3,328,633 | 6/1967 | George | 250/251 |
| 3,402,358 | 9/1968 | Wharton | 250/251 |
| 3,433,944 | 3/1969 | George | 250/251 |
| 3,641,340 | 2/1972 | Grinten et al. | 250/292 |
| 3,808,433 | 4/1974 | Fite et al. | 250/251 |

*Primary Examiner*—James W. Lawrence
*Assistant Examiner*—B. C. Anderson
*Attorney, Agent, or Firm*—Mason, Mason & Albright

[57] ABSTRACT

A hot surface detector for heavy ions following their separation on the basis of charge-to-mass ratio. Upon striking the hot surface, the heavy ions decompose and give up their lighter constituent and/or impurity atoms and molecules to the surface. Those constituent and/or impurity atoms and molecules with ionization potentials or electron affinities comparable to the work function of the hot surface become surface ionized and are emitted from the surface as a burst of either positive or negative ions which are then detected by conventional means, including detection at an electrode, by an electron multiplier or by a mass spectrometric detector for light ions. Where negative ions are to be detected, a magnetic field is applied to prevent electrons from the hot surface from reaching the detector.

17 Claims, 4 Drawing Figures

DETECTOR FOR HEAVY IONS FOLLOWING MASS ANALYSIS

RELATED APPLICATION

This is a continuation-in-part application of our application Ser. No. 319,442 filed Dec. 29, 1972 now Pat. No. 3,808,433.

BACKGROUND OF THE INVENTION

Masses of many macromolecules of biological interest, e.g., protein molecules and others with masses of the order of $10^4$ to $10^8$ amu, are not known to high accuracy. At the same time, a need exists to analyze mixtures of macromolecules in this general mass range.

Whereas it is possible to envisage applying mass spectrometric methods such as are used in the mass range below $10^4$ amu for both mass determination and analysis of mixtures of molecules and atoms, a basic problem in extending these mass spectrometric techniques to macromolecular ions lies in the detection of the ions following their analysis according to their charge-to-mass ratio.

In a conventional mass spectrometer using light ions (less than $10^4$ amu and more normally less than $10^3$ amu), the ions can be detected through secondary electron emission at a surface followed by electron multiplication in conventional electron multiplier tubes. In this method of detection, the ion is accelerated through a potential drop of about 300 volts which gives the ion a velocity of the order of $10^7$ cm/sec. This velocity is sufficient to cause secondary electron emission when the ion strikes the surface.

If the ion is heavy, however, for example $10^6$ amu as opposed to $10^3$ amu, accelerating the ion through the same potential drop provides it with a velocity much less than $10^7$ cm/sec. At this lower velocity the ion is not capable of ejecting secondary electrons from the surface with a satisfactory probability. To increase the efficiency of ejection of secondary electrons, it is necessary to increase the potential through which the heavy ion is accelerated toward the surface. However, practical limitations intrude; in order to give a heavy ion sufficient velocity to cause efficient secondary electron emission at the surface the accelerating potential difference must be of the order of millions of volts and this becomes impracticable. A need thus exists for an alternative detector for heavy ions.

Our co-pending patent application Ser. No. 319,422 discloses a method for the detection of small particulate matter and macromolecules of $10^3$ amu or greater, wherein the particulate or macromolecule strikes a heated surface. Upon striking the surface, the particulate or macromolecule decomposes and surrenders to the surface the decomposition products which include light atoms, molecules and radicals. If these decomposition products have ionization potentials or electron affinities comparable to the work function of the surface they become surface ionized and bursts of light ions of these light decomposition products are emitted from the surface. These light ions can be detected by well known conventional means for the detection of light ions.

As pointed out in patent application Ser. No. 319,442, the ions of the decomposition products are emitted from the surface in times of the order of microseconds. If a particulate or macromolecule contains a number of decomposition products which are surface ionizable, the light ions are all emitted in times of this order, and thus a burst of ions from the surface signals the arrival of a large particulate or macromolecule at the surface. The large quantity of charge contained in this burst of ions permit its being distinguished from ions from surface ionizable impurities in the material of the hot surface through the use of conventional pulse discrimination techniques.

Experiments have been performed which indicate that the method disclosed in patent application Ser. No. 319,442 readily detects particulates in the size range below 0.1 microns ($10^{-5}$ cm) in diameter, through use of calibrated filters. The signal-to-noise ratio in these experiments indicate that particulates can be detected at diameters an order of magnitude less, i.e., 0.01 microns ($10^{-6}$ cm).

A particulate or macromolecule of this size, if it has a density of approximately 1 gm/cm$^3$, as do biological molecules, it has a mass of approximately $10^{-18}$ grams, which is equal to approximately $6 \times 10^5$ amu. This is the mass range of interest for mass spectrometry of macromolcules. Thus, the methods and apparatus described in patent application Ser. No. 318,442 are applicable to detection of macromolecular ions following mass analysis.

Additional background to the invention relates to means for accomplishing the separation of ions according to their charge-to-mass ratio, prior to detection. In particular, among other means, the quadrupole mass filter invented by W. Paul and disclosed in U.S. Pat. No. 2,939,952 will accomplish the ion separation. From the well substantiated theory of quadrupole mass filters given by Professor Paul, it is readily calculable that a mass filter of pole diameter 3.6 mm, of length 30 cm, driven by an ac volage at approximately 180 kHz at a maximum amplitude of 5000 volts will analyze ions up to a mass-to-charge ratio of $10^6$ amu/electronic charge. The details of construction of such mass filters and the requisite voltage supplies are well within the state of the art.

SUMMARY OF THE INVENTION

The basic physical phenomena employed in the detector in accordance with the invention is the process of pyrolysis plus surface ionization. In this process a macromolecule, a macromolecular ion or a small particulate strikes a heated surface and decomposes into smaller fragments. These fragments may be atoms, molecules and radicals which are essential components of the macromolecule, or impurities in or on the molecule, such as might be present in the residue of a liquid in which the macromolecular was held in suspension or solution. The fragments come in contact with the heated surface and if the ionization potential of a given fragment is comparable to, which in practice means that the ionization potential is not greater than about two eV larger than, the work function of the surface, then there is a good probability that an electron will leave the fragment and enter the metal, in which case the fragment leaves the surface as a positively charge ion. If the fragment has an electron affinity comparable to the work function of the heated surface, there is a finite probability that an electron will leave the surface and become attached to the fragment, whereupon the fragment leaves the surface as a negatively charged ion. Fragments which form positive ions upon surface ionization include the alkali atoms, Li, Na, K, Rb and Cs, other metal atoms such as Mg, Ca, U, Th, and certain organic radicals and molecules. Included among fragments which formed negative ions at hot surfaces are the halogen atoms, F, Cl, Br, and I, and certain radicals, such as CN.

Surfaces which are satisfactory for positive surface ionization include tungsten, rhenium, iridium and rhodium, when operated at temperatures of from about 1000° to 2000°C. For negative ion formation, surfaces with low work functions are desired such as thoriated tungsten, tungsten carbide and materials that are used commonly in cathodes of low-temperature vacuum tubes such as mixtures of barium, calcium and strontium carbonates, barium titanates, lanthanum boride, etc.

An important aspect of the invention disclosed herein is the placement of a heated surface near the point where macromolecular ions emerge from a device such as a quadrupole mass filter which separates them according to their charge-to-mass ratio. The emerging macromolecular ions strike the surface and a burst of light fragment ions are emitted from the surface. Electromagnetic fields draw the fragment ions to a detector for the light ions where the charge carried by the ions is registered. Conventional circuitry is used: (1) to provide fields which draw the fragment ions to the detector of light ions; (2) to discriminate pulses caused by the bursts of light fragment ions as against ions of surface ionizable impurities in the hot surface itself on the basis of pulse height; and (3) to record the number or rate of pulses caused by bursts of light ions.

Other adaptabilities and capabilities of the invention will be appreciated by those skilled in the art from the following description with reference to the accompanying drawings, in which.

DESCRIPTION OF THE PREFERRED EMBODIMENTS

Figure 1:
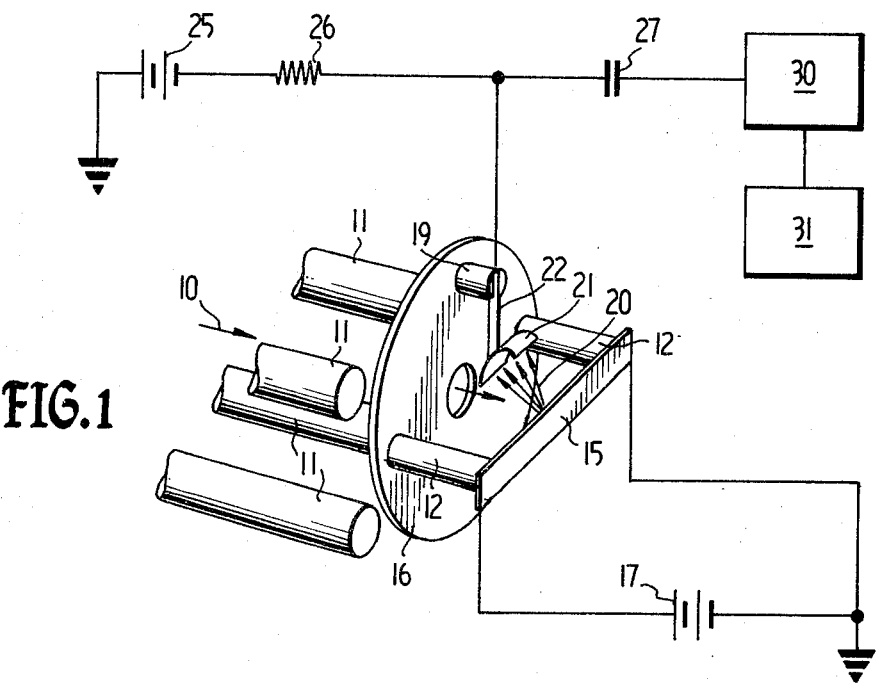
FIG. 1 is a sectional diagrammatic isometric representation of an embodiment of the invention wherein macromolecular ions previously segregated by their charge-to-mass ratio strike a hot surface to generate bursts of fragment ions directly collected by an electrode to produce discrete measurable signals.

FIG. 1 depicts a preferred embodiment of the invention. In this, and all subsequent figures, the detector devices are located within a high vacuum region (better than $10^{-4}$ mm of mercury) and the means of separating the macromolecular ions on the basis of charge-to-mass ratio is shown as a quadrupole mass filter; however, it will be understood by those skilled in the art that the invention can be utilized with other known means for separating macromolecular ions on the basis of charge-to-mass ratio.

In FIG. 1, macromolecular ions 10 are received in and pass along the axis of a quadrupole mass filter, the four poles of which are designated by reference numeral 11, and emerge through an aperture in the exit plate 16. Ions 10 then strike a surface 15 shown in the form of a ribbon which is mounted on electrically insulating supports 12 and is heated by passage therethrough of an electrical current provided by a voltage source 17. The resulting fragment ions 20 produced thereby are emitted from hot surface 15 and are drawn to a receiving electrode 21 which is mounted on an insulated support 19 via a metal rod 22 adequate to provide the necessary mechanical strength and rigidity. Fragment ions 20 are drawn to receiving electrode 21 by an electric field between hot surface 15 and the receiving electrode 21, said electric field being provided by a potential source 25 which is in excess of about two volts. In the circuit including the potential source 25 and receiving electrode 21 an impedance is provided between receiving electrode 21 and ground potential, by means of a resistor 26. The charge delivered to receiving electrode 21 by a burst of fragment ions 20 is thus not immediately passed to ground but is intially stored briefly on a condenser 27 which generates an electrical pulse passed therefrom through a pulse height discriminator 30 and then causes a scalear, count rate meter 31 or another appropriate known type of registering devices to record the arrival of macromolecular ions 10.

Figure 2:
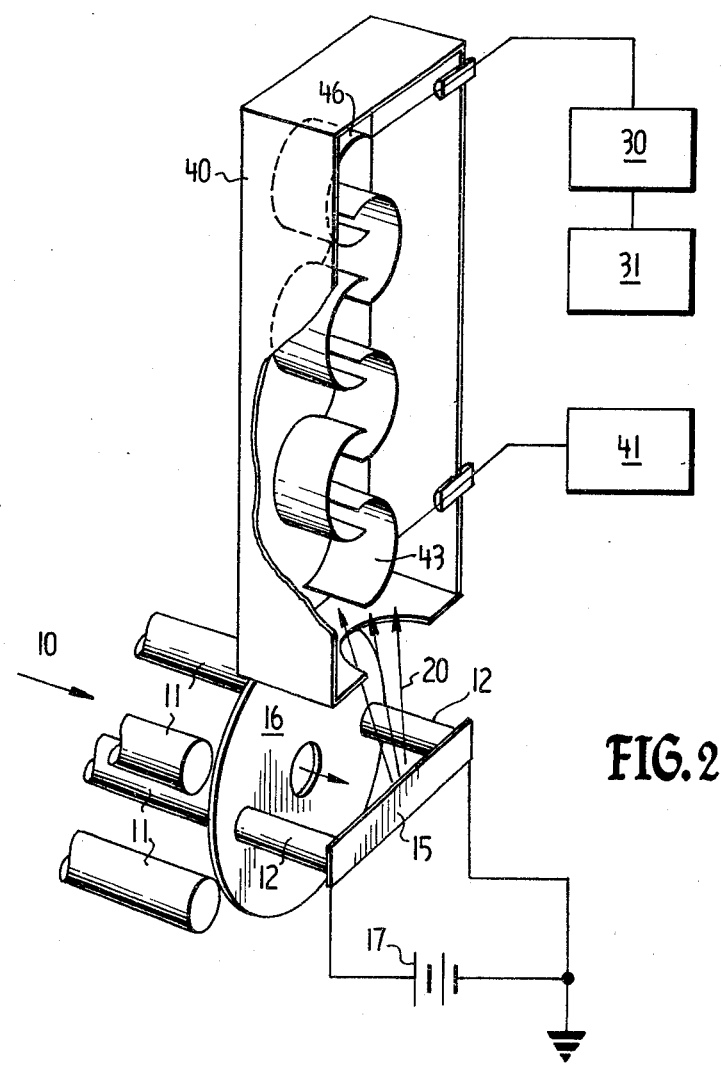
FIG. 2 is a representation similar to FIG. 1 of an embodiment including an electron multiplier to collect the bursts of fragment ions.

FIG. 2 illustrates an arrangement similar to FIG. 1, except that to increase the intensity of the electrical pulse signals, fragment ions 20 are drawn to the first dynode 43 of an electron multiplier structure 40 by a large negative potential placed on the first dynode by a voltage source 41 of in excess of at least one thousand volts. Electrons collected at the output of the electron multiplier 40 appear as a pulse of electrons and are then as described before passed through pulse height discriminator 30 to a count rate meter 31 or other appropriate device to register the arrival of macromolecular ions 10.

Figure 3:
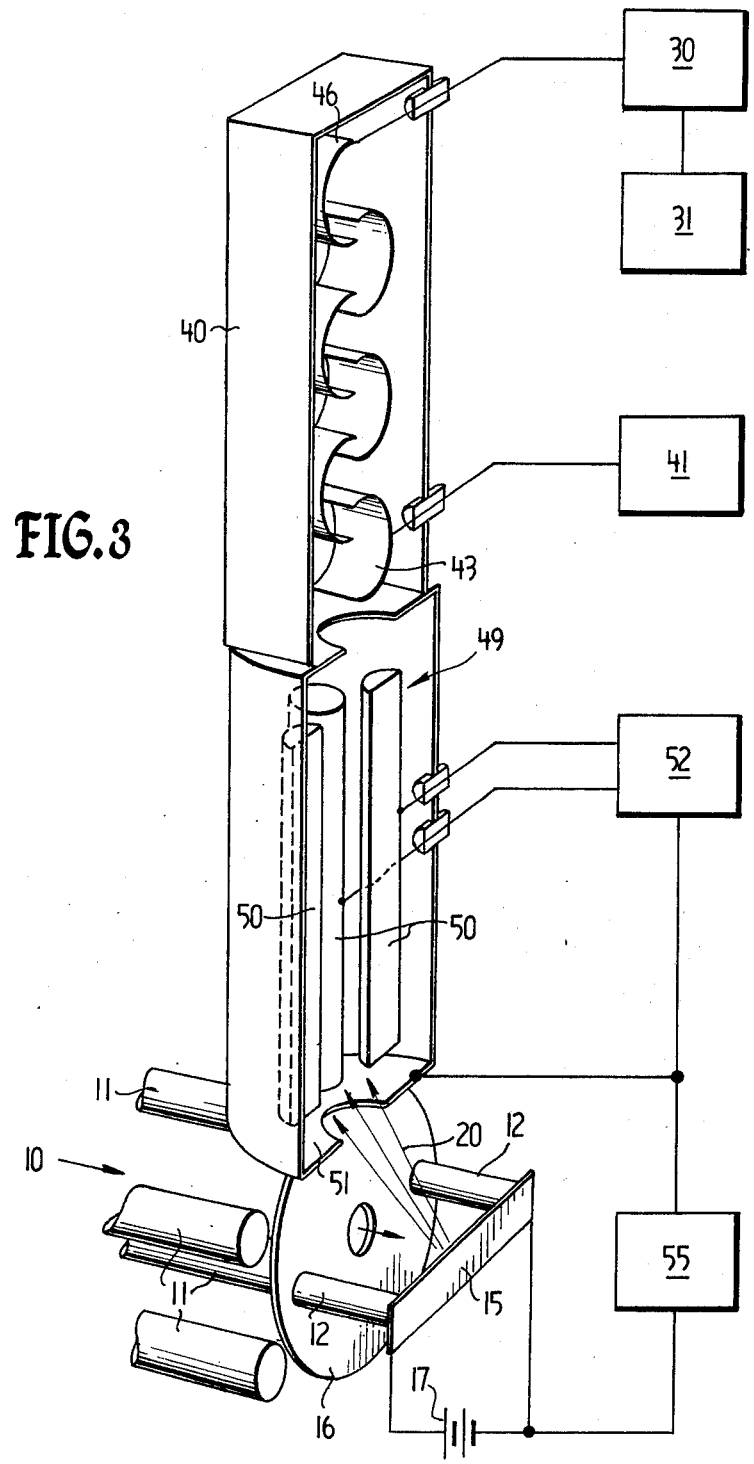
FIG. 3 is a representation similar to FIGS. 1 and 2 of an embodiment which includes a further mass filter to segregate fragment ions prior to collection by the electron multiplier.

FIG. 3 illustrates a further arrangement similar to that shown in FIGS. 1 and 2, except that prior to electron multiplier 40 provision is made for analyzing fragment ions 20 according to their mass-to-charge ratio in the interests of detecting a specific fragment ion from a macromolecular ion 10 rather than all fragment ions 20 concurrently. The means utilized for this purpose is a conventional quadrupole mass filter 49 shown in section, the four poles being designated by reference numeral 50 and the electrical means for providing the a.c. and d.c. voltages required for operation of the conventional quadrupole mass filter being designated as reference numeral 52. The entrance plate 51 of mass filter 49 is electrically biased by means of a voltage supply 55 in excess of about two volts negatively with respect to the potential of hot surface 15 to provide an electric field which accelerates fragment ions 20 into the mass filter 49. The same biasing means, voltage supply 55, is used to cause the potential along the axis of conventional mass filter 49 to be less than that potential of hot surface 15 to allow transmission of ions through the mass filter 49. It will be understood by those skilled in the art that one or more electrostatic lens may be interposed intermediate between heated surface 15 and entrance plate 51 of mass filter 49, although such a device is not shown in FIG. 3 for reasons of clarity. These fragment ions 20 with the desired charge-to-mass ratio are transmitted through mass filter 49 and then impinge on electron multiplier 40 as discussed with reference to FIG. 2.

Figure 4:
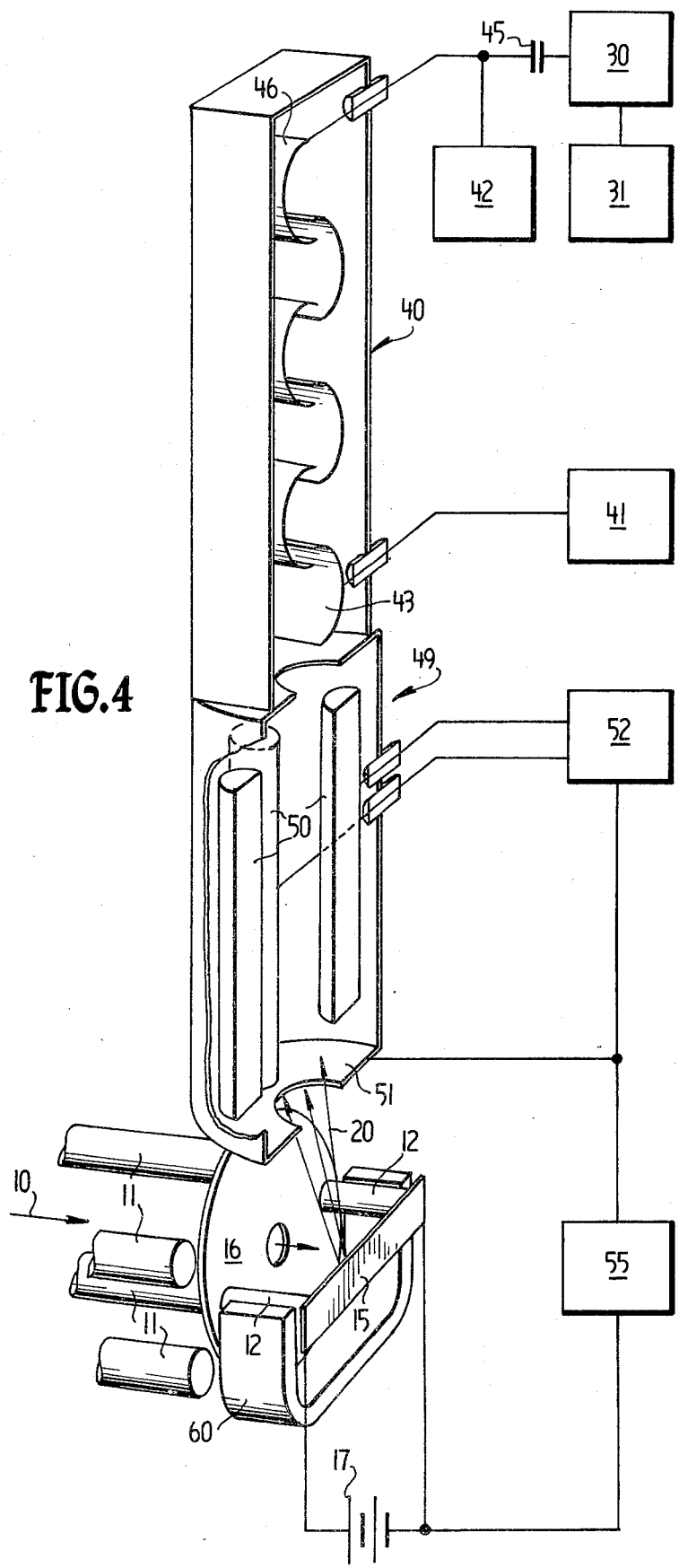
FIG. 4 is a representation similar to FIG. 3 of an embodiment of the invention which provides a magnetic field proximate the hot surface to preclude electrons from entering the mass filter.

FIG. 4 illustrates an embodiment similar to that of FIG. 3, except for the addition of means 60 to provide a magnetic field in the vicinity of hot surface 15 for the purpose of preventing electrons which might be emitted thermionically from hot surface 15 from reaching and entering mass filter 49. In this embodiment, the electrical biasing of entrance plate 51 to mass filter 49 positively with respect to the potential of hot surface 15 causes negatively ionized fragment ions 20 to be drawn into mass filter 49. For detection of negative ions, the first dynode 43 of electron multiplier 40 is placed at a high positive potential in excess of about one thousand volts by voltage supply 41 and the final electrode 46 of the multiplier is made even more positive by several thousand volts by means of a further voltage supply 42 and a blocking condenser 45 is placed between the final electrode 46 of electron multiplier 40 and pulse height discriminator 30.

It will be understood that for negative ion detection, the conventional mass filter is not a prerequisite. A means 60 for providing a magnetic field to suppress thermionic electrons may, if desired, be added to the embodiment shown in FIG. 1 and the polarity of potential source 25 is reversed. The embodiment of FIG. 2 is also suitable for negative fragment ion detection with the addition of means 60 for providing a magnetic field in the vicinity of the hot surface 15 and altering the potentials on the multiplier 40 to conform to those indicated in FIG. 4.

Having thus described our invention, what we claim as new and desire to secure by Letters Patent of the United States is;

1. A method for detecting macromolecular ions emerging from the exit end of a device which separates said macromolecular ions on the base of their charge-to-mass ratios, said method comprising the impinging of said emerging macromolecular ions having a uniform charge-to-mass ratio upon a hot surface whereupon said macromolecular ions decompose at the high temperature of the heated surface into fragments, at least some of said fragments being surface ionizable by said hot surface evolving from said hot surface as a burst of ions and discerning the burst of ions so produced by detection of its electrical charge.

2. A method in accordance with claim 1 in which the device for separating the macromolecular ions on the basis of their charge-to-mass ratio is a quadrupole mass filter.

3. A method in accordance with claim 1, wherein electric fields are provided to attract said ions evolved from said hot surface to an electrode.

4. A method in accordance with claim 1, wherein electric fields are provided to attract said ions evolved from said hot surface to the first dynode of an electron multiplier.

5. A method in accordance with claim 1, wherein said ions evolved from said hot surface are caused to pass through a device separating them on the basis of their charge-to-mass ratio prior to their detection.

6. A method in accordance with claim 5, in which the device for separating the said ions according to their charge-to-mass ratio is a quadrupole mass filter.

7. A method in accordance with claim 1, wherein said ions evolved from said hot surface are negatively charged, a magnetic field being dispersed proximate said hot surface, said magnetic field suppressing detection of electrons emitted from hot surface while permitting said negative ions to be detected.

8. A method of separating and detecting macromolecule ions which comprises the steps of separating macromolecule ions in accordance with their charge-to-mass ratios, causing macromolecule ions which have been so separated and have substantially the same charge-to-mass ratio to produce bursts of light ions by striking a heated surface, and discerning said light ions by detection of their electrical charge.

9. A method in accordance with claim 8 wherein said macromolecule ions having substantially the same charge-to-mass ratio have a mass of in excess of $10^3$ amu.

10. A method in accordance with claim 9 wherein said mass is within a range of about $10^4$ to $10^8$ amu.

11. A method in accordance with claim 8 wherein said light ions are separated in accordance with their charge-to-mass ratios and said light ions having substantially the same charge-to-mass ratio are discerned by detection of their electrical charge.

12. Apparatus for the separation and detection of macromolecule ions in excess of 1000 amu which comprises a mass filter adapted to separate said macromolecule ions in accordance with their charge-to-mass ratio, a heated surface associated with said filter whereby macromolecule ions of the same charge-to-mass ratio are conveyed by said filter to impinge on said heated surface, said surface adapted to produce a burst of light ions through surface-ionization upon the impingement thereon of one of said macromolecule ions of the same charge-to-mass ratio, and means for receiving and registering the electric charge of at least part of said burst of light ions.

13. Apparatus in accordance with claim 12 wherein said light ions are negative, magnetic field producing means disposed proximate to said heated surface for suppressing electrons emitted therefrom.

14. Apparatus in accordance with claim 12 wherein said mass filter is a quadrupole mass filter.

15. Apparatus in accordance with claim 14 wherein said means for receiving and registering the electric charge includes a further quadrupole mass filter.

16. Apparatus in accordance with claim 12 wherein said heated surface is heated on electric current passing therethrough.

17. Apparatus in accordance with claim 12 wherein said means for receiving and registering the electric charge includes a pulse height discriminator adapted to disciminate pulses generated by ions of a said burst of light ions from pulses generated by random ions evolved from said heated surface due to surface ionizable impurities therein.

* * * * *